US009546311B2

(12) United States Patent
Seeton et al.

(10) Patent No.: US 9,546,311 B2
(45) Date of Patent: Jan. 17, 2017

(54) AZEOTROPE-LIKE COMPOSITIONS OF 1,1,1,2-TETRAFLUOROPROPENE AND 1,1,1,2-TETRAFLUOROETHANE

(75) Inventors: Christopher J. Seeton, East Amherst, NY (US); Hang T. Pham, Amherst, NY (US); Rajiv R. Singh, Getzville, NY (US); Ryan Hulse, Getzville, NY (US); Mark W. Spatz, East Amherst, NY (US); David P. Wilson, East Amherst, NY (US); Samuel F. Yana Motta, East Amherst, NY (US)

(73) Assignee: HONEYWELL INTERNATIONAL INC., Morris Plains, NJ (US)

(*) Notice: Subject to any disclaimer, the term of this patent is extended or adjusted under 35 U.S.C. 154(b) by 0 days.

(21) Appl. No.: 12/542,185

(22) Filed: Aug. 17, 2009

(65) Prior Publication Data
US 2010/0047189 A1    Feb. 25, 2010

Related U.S. Application Data

(60) Provisional application No. 61/089,986, filed on Aug. 19, 2008.

(51) Int. Cl.
C09K 5/04 (2006.01)
C09K 3/30 (2006.01)
A61K 8/04 (2006.01)
A61K 8/70 (2006.01)
A61Q 19/00 (2006.01)
C08J 9/14 (2006.01)
C11D 7/50 (2006.01)

(52) U.S. Cl.
CPC .................. *C09K 3/30* (2013.01); *A61K 8/046* (2013.01); *A61K 8/70* (2013.01); *A61Q 19/00* (2013.01); *C08J 9/146* (2013.01); *C09K 5/045* (2013.01); *C11D 7/505* (2013.01); *A61K 2800/244* (2013.01); *C09K 2205/126* (2013.01); *C09K 2205/22* (2013.01); *C09K 2205/32* (2013.01)

(58) Field of Classification Search
CPC ............. C09K 5/045; C09K 2205/126; C09K 2205/22; C09K 2205/32; B01F 17/0035
See application file for complete search history.

(56) References Cited

U.S. PATENT DOCUMENTS

| | | | |
|---|---|---|---|
| 3,001,973 A | 9/1961 | Piepenbrink et al. | 260/75 |
| 3,124,605 A | 3/1964 | Wagner | 260/453 |
| 3,201,372 A | 8/1965 | Wagner | 260/77.5 |
| 3,277,138 A | 10/1966 | Holtschmidt et al. | 260/453 |
| 3,394,164 A | 7/1968 | McClellan et al. | 260/453 |
| 3,401,190 A | 9/1968 | Schmitt et al. | 260/453 |
| 3,454,606 A | 7/1969 | Brotherton et al. | 260/397.7 |
| 3,492,330 A | 1/1970 | Trecker et al. | 560/354 |
| 4,442,015 A * | 4/1984 | Packo et al. | 252/68 |
| 4,868,224 A | 9/1989 | Harasin et al. | 521/124 |
| 5,182,040 A | 1/1993 | Bartlett et al. | 252/67 |
| 5,648,017 A | 7/1997 | Bartlett et al. | 252/67 |
| 5,670,079 A * | 9/1997 | Lunger et al. | 252/67 |
| 5,714,083 A | 2/1998 | Turner | |
| 6,124,510 A | 9/2000 | Elsheikh et al. | |
| 6,258,292 B1 | 7/2001 | Turner | |
| 7,524,805 B2 | 4/2009 | Singh et al. | 510/408 |
| 2008/0069177 A1* | 3/2008 | Minor et al. | 374/4 |
| 2008/0075673 A1 | 3/2008 | Knopeck et al. | |
| 2008/0098755 A1 | 5/2008 | Singh et al. | |
| 2008/0171652 A1 | 7/2008 | Singh et al. | 502/150 |
| 2008/0230738 A1 | 9/2008 | Minor et al. | 252/67 |
| 2008/0292564 A1 | 11/2008 | Singh et al. | 424/47 |
| 2009/0127497 A1 | 5/2009 | Spatz et al. | 252/68 |
| 2009/0151365 A1 | 6/2009 | Pham et al. | 62/62 |

FOREIGN PATENT DOCUMENTS

| | | |
|---|---|---|
| JP | 04-110388 A | 4/1992 |
| WO | WO2009/047535 | 4/2009 |

OTHER PUBLICATIONS

Kim, et al., "A Study to Determine the Existence of an Azeotropic R-22 'Drop-In' Substitute," prepared by U.S. Department of Commerce for Electric Power Research Institute, Mar. 1996, pp. 1-45, U.S.
Morrison, et al., "Azeotropy in Refrigerant Mixtures," International Journal of Refrigeration, 1993, pp. 129-138, vol. 16, No. 2. U.S.

* cited by examiner

*Primary Examiner* — John Hardee
(74) *Attorney, Agent, or Firm* — Colleen D. Szuch

(57) ABSTRACT

Provided are azeotrope-like compositions consisting essentially of 1,1,1,2-tetrafluoropropene and 1,1,1,2-tetrafluoroethane and uses thereof, including use in refrigerant compositions, refrigeration systems, blowing agent compositions, and aerosol propellants.

19 Claims, No Drawings

AZEOTROPE-LIKE COMPOSITIONS OF 1,1,1,2-TETRAFLUOROPROPENE AND 1,1,1,2-TETRAFLUOROETHANE

CROSS REFERENCE TO RELATED APPLICATION

This application claims the benefit of U.S. Provisional patent application Ser. No. 61/089,986 filed Aug. 19, 2008.

BACKGROUND OF THE INVENTION

Field of the Invention

The present invention provides azeotrope-like compositions of 1,1,1,2-tetrafluoropropene (HFO-1234yf) and 1,1,1,2-tetrafluoroethane (HFC-134a), and uses thereof, including use in refrigerant compositions, refrigeration systems, blowing agent compositions, and aerosol propellants.

Description of the Related Art

Fluorocarbon based fluids have found widespread use in industry in a number of applications, including as refrigerants, aerosol propellants, blowing agents, heat transfer media, and gaseous dielectrics. Because of the suspected environmental problems associated with the use of some of these fluids, including the relatively high global warming potentials associated therewith, it is desirable to use fluids having low or even zero ozone depletion potential, such as hydrofluorocarbons ("HFCs"), and low global warming potential. Thus, the use of fluids that do not contain chlorofluorocarbons ("CFCs") or hydrochlorofluorocarbons ("HCFCs") is desirable. The use of alkenes is also desirable due to there short atmospheric lifetime which results in a relatively low global warming potential. Additionally, the use of single component fluids or azeotropic mixtures, which do not fractionate on boiling and evaporation, is desirable. However, the identification of new, environmentally-safe, non-fractionating mixtures is complicated due to the fact that azeotrope formation is not readily predictable. The industry is continually seeking new fluorocarbon based mixtures that offer alternatives, and are considered environmentally safer substitutes for CFCs and HCFCs. Of particular interest are mixtures containing hydrofluorocarbons, hydrofluoroolefins ("HFOs") and other fluorinated compounds, which have a zero ozone depletion potentials and low global warming potential. Such mixtures are the subject of this invention.

The present invention provides compositions that help to satisfy the continuing need for alternatives to CFCs and HCFCs. According to certain embodiments, the present invention provides azeotrope-like compositions comprising of 1,1,1,2-tetrafluoropropene (HFO-1234yf) and 1,1,1,2-tetrafluoroethane (HFC-134a). The preferred compositions of the invention tend to exhibit relatively low global warming potentials ("GWPs"). Accordingly, such compositions can be used to great advantage in a number of applications, including as replacements for CFCs, HCFCs, and HFCs (such as HFC-134a) in refrigerant, aerosol, blowing agents, and other applications. This azeotrope-like composition can be used as a replacement in systems already utilizing HFC-134a where a significant reduction in GWP is desired. Additionally, it has been surprisingly found that azeotrope-like compositions of HFO-1234yf and HFC-134a can be formed. Accordingly, the present invention provides methods of producing an azeotrope-like composition comprising combining HFO-1234yf and HFC-134a in amounts effective to produce an azeotrope-like composition. In addition, it has been found that the azeotrope-like compositions of the present invention exhibit properties that make that make them advantageous for use as, or in, refrigerant, aerosol, and blowing agent compositions. Accordingly, in yet other embodiments, the present invention provides refrigerant compositions comprising an azeotrope-like composition of HFO-1234yf and HFC-134a.

SUMMARY OF THE INVENTION

The invention provides an azeotrope-like composition consisting essentially of effective amounts of 1,1,1,2-tetrafluoropropene and 1,1,1,2-tetrafluoroethane to form an azeotrope-like composition.

The invention also provides a method of recharging a refrigerant system that contains a refrigerant to be replaced and a lubricant comprising the steps of: (a) removing the refrigerant to be replaced from the refrigeration system while retaining a substantial portion of the lubricant in said system; and (b) introducing to the system a refrigerant composition comprising the above azeotrope-like composition.

DETAILED DESCRIPTION OF THE INVENTION

Accordingly, the present invention provides azeotrope-like compositions comprising 1,1,1,2-tetrafluoropropene (HFO-1234yf) and 1,1,1,2-tetrafluoroethane (HFC-134a), and uses thereof, including use in refrigerant compositions, refrigeration systems, blowing agent compositions, and aerosol propellants.

As used herein, the term "azeotrope-like" is intended in its broad sense to include both compositions that are strictly azeotropic and compositions that behave like azeotropic mixtures. From fundamental principles, the thermodynamic state of a fluid is defined by pressure, temperature, liquid composition, and vapor composition. An azeotropic mixture is a system of two or more components in which the liquid composition and vapor composition are equal at the stated pressure and temperature. In practice, this means that the components of an azeotropic mixture are constant-boiling and cannot be separated during a phase change. The azeotrope-like compositions of the invention may include additional components that do not form new azeotrope-like systems, or additional components that are not in the first distillation cut. The first distillation cut is the first cut taken after the distillation column displays steady state operation under total reflux conditions. One way to determine whether the addition of a component forms a new azeotrope-like system so as to be outside of this invention is to distill a sample of the composition with the component under conditions that would be expected to separate a non-azeotropic mixture into its separate components. If the mixture containing the additional component is non-azeotrope-like, the additional component will fractionate from the azeotrope-like components. If the mixture is azeotrope-like, some finite amount of a first distillation cut will be obtained that contains all of the mixture components that is constant boiling or behaves as a single substance. It follows from this that another characteristic of azeotrope-like compositions is that there is a range of compositions containing the same components in varying proportions that are azeotrope-like or constant boiling. All such compositions are intended to be covered by the terms "azeotrope-like" and "constant boiling". As an example, it is well known that at differing pressures, the composition of a given azeotrope will vary at least slightly, as does the boiling point of the composition.

Thus, an azeotrope of A and B represents a unique type of relationship, but with a variable composition depending on temperature and/or pressure. It follows that, for azeotrope-like compositions, there is a range of compositions containing the same components in varying proportions that are azeotrope-like. All such compositions are intended to be covered by the term azeotrope-like as used herein. It is well-recognized in the art that it is not possible to predict the formation of azeotropes. (See, for example, U.S. Pat. No. 5,648,017 (column 3, lines 64-65) and U.S. Pat. No. 5,182,040 (column 3, lines 62-63), both of which are incorporated herein by reference). It has been unexpectedly discovered that HFO-1234yf and HFC-134a form azeotrope-like compositions.

According to certain preferred embodiments, the azeotrope-like compositions of the present invention comprise, and preferably consist essentially of, effective amounts of HFO-1234yf and HFC-134a. The term "effective amounts" as used herein refers to the amount of each component which upon combination with the other component, results in the formation of an azeotrope-like composition of the present invention. The azeotrope-like compositions of the present invention can be produced by combining effective amounts of HFO-1234yf and HFC-134a. Any of a wide variety of methods known in the art for combining two or more components to form a composition can be adapted for use in the present methods to produce an azeotrope-like composition. For example, HFO-1234yf and HFC-134a can be mixed, blended, or otherwise contacted by hand and/or by machine, as part of a batch or continuous reaction and/or process, or via combinations of two or more such steps. In light of the disclosure herein, those of skill in the art will be readily able to prepare azeotrope-like compositions according to the present invention without undue experimentation.

The HFO-1234yf and HFC-134a are present in amounts effective to produce an azeotrope-like composition. In one embodiment the HFO-1234yf is present in the azeotrope-like composition in an amount of from about 40 to less than 100 weight percent, preferably from about 50 to less than 90 weight percent, and more preferably from about 55 to about 80 weight percent. In one embodiment the HFC-134a, is present in the azeotrope-like composition in an amount of from greater than zero to about 60 weight percent, preferably from about 10 to about 50 weight percent, and more preferably from about 20 to about 45 weight percent. Usually the inventive azeotrope-like compositions have a boiling point of from about −30.0° C. to about −29.0° C. at a pressure of about 14.3 psia.

The present compositions have utility in a wide range of applications. For example, one embodiment of the present invention relates to blowing agent, as part of a sprayable composition such as an aerosol composition, as a cleaning composition, and refrigerant compositions, all comprising the present azeotrope-like compositions.

One embodiment of the present invention relates to a blowing agent comprising one or more azeotrope-like compositions. One embodiment of the present invention relates to methods of forming thermoset foams, and preferably polyurethane and polyisocyanurate foams. The methods generally comprise providing a blowing agent composition of the present inventions, adding (directly or indirectly) the blowing agent composition to a foamable composition, and reacting the foamable composition under the conditions effective to form a foam or cellular structure, as is well known in the art. These foams may be open cell or closed cell. Any of the methods well known in the art, such as those described in "Polyurethanes Chemistry and Technology," Volumes I and II, Saunders and Frisch, 1962, John Wiley and Sons, New York, N.Y., which is incorporated herein by reference, may be used or adapted for use in accordance with the foam embodiments of the present invention. In general, such preferred methods comprise preparing polyurethane or polyisocyanurate foams by combining an isocyanate, a polyol or mixture of polyols, a blowing agent or mixture of blowing agents comprising one or more of the present compositions, and other materials such as catalysts, surfactants, and optionally, flame retardants, colorants, or other additives.

It is convenient in many applications to provide the components for polyurethane or polyisocyanurate foams in pre-blended formulations. Most typically, the foam formulation is pre-blended into two components. The isocyanate and optionally certain surfactants and blowing agents comprise the first component, commonly referred to as the "A" component. The polyol or polyol mixture, surfactant including silicone surfactants, catalysts including amine catalysts, blowing agents, flame retardant, and other isocyanate reactive components comprise the second component, commonly referred to as the "B" component. The blowing agent comprises the azeotrope-like composition of this invention and optionally a hydrocarbon, halogenated hydrocarbon, $CO_2$ generating material, or combinations thereof. Preferably the halogenated hydrocarbon comprises a chlorofluorocarbon, hydrochlorofluorocarbon, hydrofluorocarbon, or combinations thereof. The blowing agent component is usually present in the polyol premix composition in an amount of from about 1 wt. % to about 30 wt. %, by weight of the polyol premix composition. The polyol component, can be any polyol which reacts in a known fashion with an isocyanate in preparing a polyurethane or polyisocyanurate foam. Useful polyols comprise one or more of a sucrose containing polyol; phenol, a phenol formaldehyde containing polyol; a glucose containing polyol; a sorbitol containing polyol; a methylglucoside containing polyol; an aromatic polyester polyol; glycerol; ethylene glycol; diethylene glycol; propylene glycol; graft copolymers of polyether polyols with a vinyl polymer; a copolymer of a polyether polyol with a polyurea; or combinations thereof. The polyol component is usually present in the polyol premix composition in an amount of from about 60 wt. % to about 95 wt. %, by weight of the polyol premix composition. The polyol premix composition next contains a surfactant component which silicone surfactant and optionally an additional non-silicone surfactant. The surfactant is usually present in the polyol premix composition in an mount of from about 0.5 wt. % to about 5.0 wt. % by weight of the polyol premix composition. The polyol premix composition next contains a catalyst which is preferably an amine. Tertiary amines are preferred. Preferred amines include: N,N-dimethylcyclohexylamine, dimethlyethanolamine, N,N,N',N',N",N"'-pentamethyldiethylenetriamine, 1,4-diaza-bicyclo[2.2.2]octane (DABCO), and triethylamine. The catalyst is usually present in the polyol premix composition in an amount of from about 0.1 wt. % to about 3.5 wt. % by weight of the polyol premix composition.

A foamable composition suitable for forming a polyurethane or polyisocyanurate foam may be formed by reacting an organic polyisocyanate and the polyol premix composition described above. Any organic polyisocyanate can be employed in polyurethane or polyisocyanurate foam synthesis inclusive of aliphatic and aromatic polyisocyanates. Suitable organic polyisocyanates include aliphatic, cycloaliphatic, araliphatic, aromatic, and heterocyclic isocyanates which are well known in the field of polyurethane chemistry.

These are described in, for example, U.S. Pat. Nos. 4,868,224; 3,401,190; 3,454,606; 3,277,138; 3,492,330; 3,001,973; 3,394,164; 3,124.605; and 3,201,372. Preferred as a class are the aromatic polyisocyanates. Representative organic polyisocyanates correspond to the formula:

R(NCO)z wherein R is a polyvalent organic radical which is either aliphatic, aralkyl, aromatic or mixtures thereof, and z is an integer which corresponds to the valence of R and is at least two.

Accordingly, polyurethane or polyisocyanurate foams are readily prepared by bringing together the A and B side components either by hand mix for small preparations and, preferably, machine mix techniques to form blocks, slabs, laminates, pour-in-place panels and other items, spray applied foams, froths, and the like. Optionally, other ingredients such as fire retardants, colorants, auxiliary blowing agents, and even other polyols can be added as a third stream to the mix head or reaction site. Most preferably, however, they are all incorporated into one B-component as described above. Conventional flame retardants can also be incorporated, preferably in amount of not more than about 20 percent by weight of the reactants.

The present methods and systems also include forming a one component foam, preferably polyurethane foam, containing a blowing agent in accordance with the present invention. In certain preferably embodiments, a portion of the blowing agent is contained in the foam forming agent, preferably by being dissolved in a foam forming agent which is liquid at the pressure within the container, a second portion of the blowing agent is present as a separate gas phase. In such systems, the contained/dissolved blowing agent performs, in large part, to cause the expansion of the foam, and the separate gas phase operates to impart propulsive force to the foam forming agent. Such one component systems are typically and preferably packaged in a container, such as an aerosol type can, and the blowing agent of the present invention thus preferably provides for expansion of the foam and/or the energy to transport the foam/foamable material from the package, and preferably both. In certain embodiments, such systems and methods comprise charging the package with a fully formulated system (preferably isocyanate/polyol system) and incorporating a gaseous blowing agent in accordance with the present invention into the package, preferably an aerosol type can.

In addition to the previously described ingredients, other ingredients such as, dyes, fillers, pigments and the like can be included in the preparation of the foams. Dispersing agents and cell stabilizers can be incorporated into the present blends. Conventional fillers for use herein include, for example, aluminum silicate, calcium silicate, magnesium silicate, calcium carbonate, barium sulfate, calcium sulfate, glass fibers, carbon black and silica. The filler, if used, is normally present in an amount by weight ranging from about 5 parts to 100 parts per 100 parts of polyol. A pigment which can be used herein can be any conventional pigment such as titanium dioxide, zinc oxide, iron oxide, antimony oxide, chrome green, chrome yellow, iron blue siennas, molybdate oranges and organic pigments such as para reds, benzidine yellow, toluidine red, toners and phthalocyanines. The polyurethane or polyisocyanurate foams produced can vary in density from about 0.5 pounds per cubic foot to about 60 pounds per cubic foot, preferably from about 1.0 to 20.0 pounds per cubic foot, and most preferably from about 1.5 to 6.0 pounds per cubic foot. The density obtained is a function of how much of the blowing agent or blowing agent mixture disclosed in this invention plus the amount of auxiliary blowing agent, such as water or other co-blowing agents is present in the A and/or B components, or alternatively added at the time the foam is prepared. These foams can be rigid, flexible, or semi-rigid foams, and can have a closed cell structure, an open cell structure or a mixture of open and closed cells. These foams are used in a variety of well known applications, including but not limited to thermal insulation, cushioning, flotation, packaging, adhesives, void filling, crafts and decorative, and shock absorption.

It is also possible to produce thermoplastic foams using the compositions of the invention. For example, conventional polystyrene and polyethylene formulations may be combined with the compositions in a conventional manner to produce rigid foams Examples of thermoplastic foam components include polyolefins, such as for example polystyrene. Other examples of thermoplastic resins include polyethylene, ethylene copolymers, polypropylene, and polyethyleneterephthalate. In certain embodiments, the thermoplastic foamable composition is an extrudable composition. It is also generally recognized that the thermoplastic foamable composition may include adjuvants such as nucleating agents, flame or fire retardant materials, cell modifiers, cell pressure modifiers, and the like.

With respect to thermoplastic foams, the preferred methods generally comprise introducing a blowing agent in accordance with the present invention into a thermoplastic material, and then subjecting the thermoplastic material to conditions effective to cause foaming. For example, the step of introducing the blowing agent into the thermoplastic material may comprise introducing the blowing agent into a screw extruder containing a thermoplastic polymer, and the step of causing foam may comprise lowering the pressure on the thermoplastic material and thereby causing expansion of the blowing agent and contributing to the foaming of the material. Suitable thermoplastic polymers non-exclusively include polystyrene, polyethylene, polypropylene, polyethylene terephthalate, and combinations of these. It will be generally appreciated by those skilled in the art, especially in view of the disclosure herein, that the order and manner in which the blowing agent of the present invention is formed and/or added to the foamable composition does not generally affect the operability of the present invention thermoset or thermoplastic foams. It is contemplated also that in certain embodiments it may be desirable to utilize the present compositions when in the supercritical or near supercritical state as a blowing agent.

The azeotrope-like compositions of this invention may also be used as refrigerant compositions. The refrigerant compositions of the present invention may be used in any of a wide variety of refrigeration systems including air-conditioning, refrigeration, heat-pump systems, and the like. In certain preferred embodiments, the compositions of the present invention are used in refrigeration systems originally designed for use with an HFC refrigerant, such as, for example, HFC-134a. The preferred compositions of the present invention tend to exhibit many of the desirable characteristics of HFC-134a and other HFC-refrigerants, including non-flammability or low flammability, and a GWP that is as low, or lower than that of conventional HFC-refrigerants. In addition, the relatively constant boiling nature of the compositions of the present invention makes them even more desirable than certain conventional HFCs for use as refrigerants in many applications.

In certain embodiments, the compositions of the present invention may be used to retrofit refrigeration systems containing a refrigerant which comprises a chlorofluorocarbon, a hydrofluorocarbon, a hydrochlorofluorocarbon, a chlorofluorcarbon, or combinations thereof and lubricants conventionally used therewith. Such as a mineral oil, alkybenezene (AB), polyalphaolefin (PAO), polyol ester (POE), polyakylene glycol (PAG), polyvinyl ether (PVE), synthetic naphthalene, fluorolubricant or combinations thereof. The method comprises removing or leaking at least a portion of the refrigerant from the refrigeration apparatus and leaving a residue comprising the lubricant, and adding to said residue the inventive azeotrope-like composition. Preferred refrigeration compositions of the present invention may be used in refrigeration systems containing a lubricant used conventionally with CFC HCFC, and/or CFC-refrigerants, such as mineral oils, silicone oils, and the like, or may be used with other lubricants traditionally used with such refrigerants. Preferably, the present methods involve recharging a refrigerant system that contains a refrigerant to be replaced and a lubricant comprising the steps of (a) removing the refrigerant to be replaced from the refrigeration system while retaining a substantial portion of the lubricant in said system; and (b) introducing to the system a composition of the present invention. As used herein, the term "substantial portion" refers generally to a quantity of lubricant which is at least about 50% (by weight) of the quantity of lubricant contained in the refrigeration system prior to removal of the refrigerant. Preferably, the substantial portion of lubricant in the system according to the present invention is a quantity of at least about 60% of the lubricant contained originally in the refrigeration system, and more preferably a quantity of at least about 70%. As used herein the term "refrigeration system" refers generally to any system or apparatus, or any part or portion of such a system or apparatus, which employs a refrigerant to provide cooling to one space thereby heating another. Such refrigeration systems include, for example, air conditioners including automotive air conditioning, electric refrigerators, chillers, transport refrigeration systems, commercial refrigeration systems and the like. Refrigeration systems may also include heat pump systems where as the desired benefit is the heating provided by condensing the refrigerant stream and the cooling portion or evaporator extracts heat from the surroundings or other energy streams for use in such heating.

Any of a wide range of known methods can be used to remove refrigerants to be replaced from a refrigeration system while removing less than a major portion of the lubricant contained in the system. For example, because refrigerants are quite volatile relative to traditional hydrocarbon-based lubricants, such as mineral oil, alkybenezene (AB), polyalphaolefins (PAO), polyol esters (POE), polyakylene glycols (PAG), fluorolubricants and the like (the boiling points of refrigerants are generally less than 10° C. whereas the boiling points of lubricants are generally more than 200° C.). In embodiments wherein the lubricant is a hydrocarbon-based lubricant, the removal step may readily be performed by pumping refrigerants in the gaseous state out of a refrigeration system containing liquid state lubricants. Such removal can be achieved in any of a number of ways known in the art, including, the use of a refrigerant recovery system, such as the recovery system manufactured by Robinair of Ohio. Alternatively, a cooled, evacuated refrigerant container can be attached to the low pressure side of a refrigeration system such that the gaseous refrigerant is drawn into the evacuated container and removed. Moreover, a compressor may be attached to a refrigeration system to pump the refrigerant from the system to an evacuated container. In light of the above disclosure, those of ordinary skill in the art will be readily able to remove the system refrigerant charge without removing the majority of the lubricant and charging with the disclosed azeotrope-like blend of HFC-134a and HFO-1234yf according to the present invention.

Another way for which refrigerant may be removed from the system is in the case of leaks, hose permeation or system failure in which an operator does not play an active part in the refrigerant removal, but rather the nature of the system seal, materials of construction, or operating conditions cause refrigerant removal. In this case if an operator "tops off" a system where as the full refrigerant charge has not yet been removed. This is common practice in automotive air conditioning systems where the user experiences decreased performance and a service shops or the home user themselves recharge the system, pulling either HFO-1234yf into a system originally designed HFC-134a or pulling HFC-134a into a system originally designed for HFO-1234yf. This would constitute a partial charge, but would allow for azeotrope-like blend of HFC-134a and HFO-1234yf according to the present invention. Any of a wide range of methods for introducing the present refrigerant compositions to a refrigeration system can be used in the present invention. For example, one method comprises attaching a refrigerant container to the low-pressure side of a refrigeration system and turning on the refrigeration system compressor to pull the refrigerant into the system. In such embodiments, the refrigerant container may be placed on a scale such that the amount of refrigerant composition entering the system can be monitored. When a desired amount of refrigerant composition has been introduced into the system, charging is stopped. Alternatively, a wide range of charging tools, known to those of skill in the art, is commercially available. Accordingly, in light of the above disclosure, those of skill in the art will be readily able to introduce the refrigerant compositions of the present invention into refrigeration systems according to the present invention without undue experimentation.

According to certain other embodiments, the present invention provides refrigeration systems comprising a refrigerant of the present invention and methods of producing heating or cooling by condensing and/or evaporating a composition of the present invention. In certain preferred embodiments, the methods for cooling an article according to the present invention comprise condensing a refrigerant composition comprising an azeotrope-like composition of the present invention and thereafter evaporating said refrigerant composition in the vicinity of the article to be cooled. Certain preferred methods for heating an article comprise condensing a refrigerant composition comprising an azeotrope-like composition of the present invention in the vicinity of the article to be heated and thereafter evaporating said refrigerant composition. In light of the disclosure herein, those of skill in the art will be readily able to heat and cool articles according to the present inventions without undue experimentation.

In another embodiment, the azeotrope-like compositions of this invention may be used as propellants in sprayable compositions, either alone or in combination with known propellants. The propellant composition comprises, more preferably consists essentially of, and, even more preferably, consists of the azeotrope-like compositions of the invention. The active ingredient to be sprayed together with inert ingredients, solvents, and other materials may also be present in the sprayable mixture. Preferably, the sprayable composition is an aerosol. Suitable active materials to be sprayed include, without limitation, cosmetic materials such as a deodorant, a perfume, and a hair spray; cleansers, a wax, a defluxing agent, a polishing agent a room freshener, an insecticide, a cooking oil, as well as a drug or other biologically active material including medicinal materials such as anti-asthma and anti-halitosis medications, or combinations of any of the foregoing. Other uses of the present azeotrope-like compositions include use as solvents, cleaning agents, and the like. Those skilled in the art will be readily able to adapt the present compositions for use in such applications without undue experimentation.

EXAMPLES

The following non-limiting examples serve to illustrate the invention.

Example 1

An ebulliometer consisting of vacuum jacketed tube with a condenser on top which is further equipped with a Quartz Thermometer is used. About 17.41 g of HFO-1234yf is charged to the ebulliometer and then HFC-134a is added in small, measured increments. Temperature depression is observed when HFC-134a is added to HFO-1234yf, indicating a binary minimum boiling azeotrope is formed. From greater than about 0 to about 60 weight percent HFC-134a, the boiling point of the composition stays below or around the boiling point of HFO-1234yf. The normal boiling temperature of HFC-134a is about −26.3° C. The binary mixtures shown in Table 1 show the boiling point of the compositions did not go above the boiling point of HFO-1234yf. The compositions exhibit azeotrope and/or azeotrope-like properties over this range.

TABLE 1

| HFO-1234yf/HFC-134a Compositions at 14.3 psia | | |
|---|---|---|
| T (° C.) | Wt. % HFO-1234yf | Wt. % HFC-134a |
| −28.97 | 100.0 | 0.00 |
| −29.13 | 97.81 | 2.19 |
| −29.63 | 89.83 | 10.17 |
| −29.66 | 86.27 | 13.73 |
| −29.86 | 75.89 | 24.11 |
| −29.91 | 71.29 | 28.71 |
| −29.92 | 65.16 | 34.84 |
| −29.91 | 60.68 | 39.32 |
| −29.81 | 56.27 | 43.73 |
| −29.67 | 52.71 | 47.29 |
| −29.38 | 47.10 | 52.90 |
| −29.16 | 43.38 | 56.62 |

Example 2

An azeotrope-like composition (50/50 by mass) of HFO-1234yf and HFC-134a was charged into an instrumented automotive air condition system and tested under the conditions typical for normal operation. The conditions are specified in a Society of Automotive Engineers (SAE) Standard J2765 as conditions experienced during operation of a motor vehicle. The system was evaluated at conditions representing full load cooling for ambient temperatures of 35, 45 and 50° C. as to exclude compressor cycling and system control influence of the results. Table 2 illustrates results from such testing. Lower discharge temperatures and higher suction pressures make this azeotrope-like blend attractive in refrigeration and heat pump operation. The lower discharge temperature adds robustness in thermal stability of system lubricants, materials and the refrigerant itself. The higher suction pressure competes against the higher discharge pressure of the mixtures; however, this allows for further heat exchanger optimization to achieve energy usage savings.

TABLE 2

Results of MAC testing with azeotrope-like compositions of HFO-1234yf and HFC-134a

| | | Condition* | | | | | | |
|---|---|---|---|---|---|---|---|---|
| | | I45 | M45 | H45 | I50 | I35 | M35 | H35 |
| Discharge Temperature, ° C. | Blend | 79.8 | 90.47 | 103.4 | 88.4 | 74.6 | 87.9 | 101.1 |
| | HFC-134a Alone | 89.7 | 105.7 | 121.0 | 97.2 | 82.6 | 99.3 | 113.5 |
| | HFO-1234yf Alone | 80.2 | 93.0 | 105.4 | 87.6 | 73.8 | 88.4 | 101.5 |
| Discharge Pressure, MPa | Blend | 1.94 | 2.02 | 1.99 | 2.21 | 1.65 | 1.73 | 1.71 |
| | HFC-134a Alone | 1.91 | 1.92 | 1.90 | 2.20 | 1.60 | 1.63 | 1.63 |
| | HFO-1234yf Alone | 1.82 | 1.87 | 1.86 | 2.06 | 1.53 | 1.59 | 1.89 |
| Evaporation Temperature, ° C. | Blend | 9.4 | 2.4 | −0.2 | 13.1 | 10.5 | 2.6 | −0.1 |
| | HFC-134a Alone | 9.3 | 2.5 | 0.9 | 12.9 | 10.7 | 3.8 | 2.0 |
| | HFO-1234yf Alone | 10.0 | 3.9 | 2.2 | 13.0 | 10.8 | 4.5 | 3.0 |

TABLE 2-continued

Results of MAC testing with azeotrope-like compositions of HFO-1234yf and HFC-134a

| | | Condition* | | | | | | |
|---|---|---|---|---|---|---|---|---|
| | | I45 | M45 | H45 | I50 | I35 | M35 | H35 |
| Suction Pressure, kPa | Blend | 432 | 316 | 275 | 487 | 446 | 314 | 272 |
| | HFC-134a Alone | 383 | 267 | 235 | 434 | 403 | 277 | 238 |
| | HFO-1234yf Alone | 404 | 294 | 258 | 446 | 411 | 293 | 253 |
| System Cooling Capacity, kW | Blend | 4.13 | 6.47 | 8.16 | 4.40 | 5.10 | 7.51 | 9.55 |
| | HFC-134a Alone | 4.26 | 6.67 | 8.22 | 4.51 | 5.12 | 7.97 | 9.71 |
| | HFO-1234yf Alone | 4.26 | 6.59 | 8.25 | 4.42 | 4.97 | 7.68 | 9.52 |
| System Efficiency, COP (kW/kW) | Blend | 2.1 | 1.3 | 1.1 | 2.0 | 2.9 | 1.7 | 1.4 |
| | HFC-134a Alone | 2.3 | 1.5 | 1.1 | 2.2 | 3.1 | 1.8 | 1.4 |
| | HFO-1234yf Alone | 2.2 | 1.4 | 1.1 | 2.1 | 3.0 | 1.7 | 1.3 |

*Condition are specified by SAE Standard J2765 wherein:
I35 = automobile idling at 35° C. ambient temperature.
I45 = automobile idling at 45° C. ambient temperature.
I50 = automobile idling at 50° C. ambient temperature.
M35 = automobile at medium speeds of 35-45 mph at 35° C. ambient temperature.
M45 = automobile at medium speeds of 35-45 mph at 45° C. ambient temperature.
H35 = automobile at high speeds of 65-80 mph at 35° C. ambient temperature.
H45 = automobile at high speeds of 65-80 mph at 45° C. ambient temperature.
The compositions are HFC-134a Alone, HFO-1234yf Alone and 50/50 by mass blends of HFC-134a and HFO-1234yf.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A non-flammable composition consisting essentially of from about 56 weight percent to about 65 weight percent of 1,1,1,2-tetrafluoropropene and from about 35 weight percent to about to about 44 weight percent of 1,1,1,2-tetrafluoroethane to form a non-flammable composition, said composition being azeotropic at at least one concentration of the components within said range of component concentrations, said non-flammable composition having a boiling point that is below the boiling point of said 1,1,1,2-tetrafluoropropene and said 1,1,1,2-tetrafluoroethane and that is from about −29.81° C. to about −29.92° C. at a pressure of about 14.3 psia.

2. The composition of claim 1 which consists essentially of about 40 weight percent 1,1,1,2-tetrafluoroethane and about 60 weight percent of 1,1,1,2-tetrafluoropropene.

3. The composition of claim 1 which consists of about 40 weight percent 1,1,1,2-tetrafluoroethane and about 60 weight percent of 1,1,1,2-tetrafluoropropene.

4. A solvent consisting essentially of the composition of claim 1.

5. A blowing agent consisting essentially of a composition of claim 1.

6. A foam premix composition comprising a polyol and blowing agent of claim 5.

7. A foam comprising a plurality of polymeric cells and a composition contained in at least one of said cells, said composition comprising a blowing agent of claim 5.

8. A foamable composition comprising and at least one thermoset foam component and a blowing agent consisting essentially of a composition of claim 1.

9. The foamable composition of claim 8, wherein said at least one thermoset component comprises a composition capable of forming a polyurethane foam, a phenolic foam, or a polyisocyanurate foam.

10. A foamable composition comprising at least one thermoplastic foam component and a blowing agent consisting essentially of a composition of claim 1.

11. The foamable composition of claim 10 wherein said thermoplastic foam component comprises a polystyrene, polyethylene, polypropylene, polyethyleneterephthalate, and combinations of these.

12. A sprayable composition comprising a material to be sprayed and a propellant consisting essentially of a composition of claim 1.

13. A sprayable composition according to claim 12 wherein the material to be sprayed comprises a drug, a biologically active material, a deodorant, a perfume, a hair spray, a cleanser, a wax, a defluxing agent, a polishing agent, a room freshener, an insecticide, a cooking oil, or combinations thereof.

14. A refrigerant composition comprising the composition of claim 1.

15. A method for cooling an article which comprises condensing a refrigerant composition of claim 14 and thereafter evaporating said refrigerant composition in the vicinity of the article to be cooled.

16. A method for heating an article which comprises condensing a refrigerant composition of claim 14 in the vicinity of the article to be heated and thereafter evaporating said refrigerant composition.

17. A method of recharging a refrigerant system that contains a refrigerant to be replaced and a lubricant comprising the steps of: (a) removing the refrigerant to be replaced from the refrigeration system while retaining a substantial portion of the lubricant in said system; and (b) introducing to the system a refrigerant composition of claim 14.

18. A method for modifying a refrigeration apparatus which refrigeration apparatus comprises a refrigerant and a lubricant, which refrigerant comprises a chlorofluorocarbon, a hydrofluorocarbon, a hydrochlorofluorocarbon, a chlorofluorcarbon, or combinations thereof, and the lubricant comprises a mineral oil, alkybenezene, polyalphaolefin, polyol ester, polyakylene glycol, polyvinyl ether, synthetic naphthalene, fluorolubricant or combinations thereof, the method comprising removing or leaking at least a portion of the refrigerant from the refrigeration apparatus and leaving a residue comprising the lubricant, and adding to said residue a composition consisting essentially of the composition of claim 1.

19. A refrigeration system comprising a refrigerant consisting essentially of the composition of claim 1.

\* \* \* \* \*